United States Patent [19]  
Juni

[11] 3,930,956  
[45] Jan. 6, 1976

[54] METHOD FOR THE GENETIC DETECTION OF MICROORGANISMS
[75] Inventor: Elliot Juni, Ann Arbor, Mich.
[73] Assignee: The Regents of the University of Michigan, Ann Arbor, Mich.
[22] Filed: Oct. 29, 1973
[21] Appl. No.: 410,533

[52] U.S. Cl. ................................. 195/103.5 R
[51] Int. Cl.² ........................................ C12K 1/04
[58] Field of Search ............ 195/103.5 R, 2, 65, 96, 195/75, 28 N

[56] References Cited
OTHER PUBLICATIONS
J. Gen. Microbiol., (1969), 57, pp. 125–130.
J. Gen. Microbiol., (1961), 26, pp. 303–312.

Primary Examiner—A. Louis Monacell
Assistant Examiner—C. A. Fan
Attorney, Agent, or Firm—Olsen and Stephenson

[57] ABSTRACT

A method for the genetic detection of specific microorganisms based on the phenomenon of transformation is disclosed. Variants such as auxotrophs which are distinguishable from their wild, parent strain are transformed by deoxyribonucleic acid (DNA) extracted from microorganism cells present in a biological test sample. The detection of transformed cells indicates the presence of the specific microorganism under determination in the sample. The transforming-DNA is in a sterile, crude form, thereby providing a simple, rapid, and highly specific test method.

34 Claims, No Drawings

METHOD FOR THE GENETIC DETECTION OF MICROORGANISMS

The invention described herein was made in the course of work under a grant from the National Institutes of Health, Department of Health, Education and Welfare.

BACKGROUND OF THE INVENTION

1. Field of the Invention

The present invention relates to means for detecting and identifying microorganisms in biological samples. In particular, the present invention relates to the specific genetic detection of microorganisms based on the transformation phenomenon. The present invention also relates to methods of preparing extracts of deoxyribonucleic acid from microorganisms in biological samples which are useful in such a transformation assay.

Transformation is the heritable modification of the properties of one strain of microorganism (acceptor) by deoxyribonucleic acid (DNA) extracted from the cells of another strain of microorganism (donor). The genes carried from the donor cells to the acceptor cells are incorporated into the chromosome of the acceptor cells replacing their corresponding alleles. A variant which is distinguishable from its wild, parent strain in one or more characteristics is transformed by DNA from the parent strain to form a transformant strain in which one or more of the distinguishing characteristics of the variant has disappeared and has been replaced by the corresponding characteristic of the parent strain.

For instance, an auxotroph is a mutant which differs from its parent strain in its nutrient requirements. The auxotroph requires at least one more nutrient for growth which is not required by its parent strain. DNA from the parent strain transforms the auxotroph into a transformant strain which requires no more nutrients than required by the parent strain. Such a transformant is maned a prototroph.

2. Description of the Prior Art

Since the serendipitous discovery of the transformation phenomenon in 1928, the scientific community has primarily been concerned with verifying the role of DNA as the substance which causes transformation to occur and with the use of the transformation phenomenon in studying the mechanisms of genetics. DNA is now overwhelmingly held to be the transformation-causing substance. This conclusion is based on exhaustive research efforts aimed at isolating and highly purifying each cellular component and attempting to induce transformation using the resulting highly pure homogenous extracts. Up until the publication of certain aspects of the present invention in the *J. Bacteriol.* 112(2): 917(197), all of the prior art involving the principle of DNA-extracted transformations taught that only either virtually pure DNA or DNA obtained following involved procedures could be used to induce transformation in microorganisms. Publications relating to this teaching are *J. Mol. Biol.* 3.208(1961), *J. gen. Microbiol.* 37.341(1964), and Hayes, W. *The Genetics of Bacteria and Their Viruses*, John Wiley and Sons, Inc. (New York 1964) p. 55.

At the present time, the detection and identification of microorganisms ususally involve tedious compilations of data relating to the characteristics of the particular microorganism being studied. Characteristics that are generally studied include the morphology of colonies, the ability of the microorganism to ferment various carbohydrates, and many more. Even on the basis of as many as 25 tests to determine characteristics exhibited by the particular microorganism being studied, a highly skilled taxonomist still must, at times, be satisfied with making an educated guess as to the identity of the microorganism. In terms of clinical diagnosis, this conventional procedure has limited utility since in order that characteristics can be identified with a homogenous colony, pure isolates must be prepared from each test sample and numerous characterising tests must be performed, and yet the taxonomist must qualify his conclusion as to the identity of the microorganism.

While the transformation phenomenon has been known for several decades, it has not been found useful in the clinical detection of microorganisms because of the technical complexities involved in conventional transformation procedures. Standard DNA purifications are highly complicated procedures requiring on the average about 3 days to complete.

In the diagnosis of microbial derived disease, the accurate identification of the microorganism involved often is essential to proper and effective treatment. The conventional taxonomical methods are burdened with inherent error factors and in many cases confuse rather than clarify a patient's condition. A particular case in which specific identification is urgently needed is in the detection of *Neisseria gonnorhoeae*. Colonies of this virulent microorganism are easily mistaken for less harmful bacteria following the conventional taxonomical methods.

A determination based solely on genetics is the only true means of detecting and identifying microorganisms. It is a truism that microorganisms are what they are because of their genetic composition. The clinician presently lacks what would be his most useful tool for diagnosing microbial derived diseases, the rapid genetic determination of microorganisms.

SUMMARY OF THE INVENTION

It has now been found that crude, cell-extracted deoxyribonucleic acid (DNA) can be used in the specific detection of microorganisms using a transformation assay technique. Biological samples containing several different types of microorganisms can be rapidly assayed without interference from extraneous material present in the crude extract of DNA. Extraneous material which may be present in the crude extract of DNA includes any material, other than the DNA extracted from microorganism cells of the strain to be detected, which does not deleteriously affect, at its concentration in the extract, either the DNA extracted from microorganism cells of the strain to be detected or the variant cells as they are contacted by the crude extract of DNA in step (b). Thus, such extraneous material includes DNA extracted from microorganism cells of stains other than the one being detected; non-viable microorganism cells; extraneous cellular material such as cell wall and intracellular constituents, which include various proteins, carbohydrates, glycoproteins, lipids, lipoproteins, and glycolipids; atmospheric contaminants; and materials which appear in the extract as a result of the extracting process, such as the substances present in the surfactant solution where a surfactant is used to lyse the cells. Since the transformation mechanism has been found to be unimpaired by the presence of such extraneous cellular material, samples which contain cells of microorganisms other than the particular microorganism under study may be assayed using the present method. The choice of a particular variant for exposure to the crude extract of DNA determines the specificity of the microorganism strain being assayed.

The present method basically comprises the following steps: (a) preparing a sterile, crude extract comprising deoxyribonucleic acid endogenous to microorganism cells present in the biological sample to be assayed; (b) contacting a viable, transformable variant of the specific microorganism to be detected, such as a mutant, with the crude extract to form a mixture, the specific microorganism possessing a distinguishing characteristic relative to the variant; and (c) subjecting the mixture to an analysis for detecting the presence of the distinguishing characteristic. The appearance of this distinguishing characteristic is the direct result of the transformation of variant cells into transformant cells which possess the distinguishing characteristic and thereby is indicative of the presence of the specific microorganism in the sample from which the crude extract of DNA was obtained. The viable variant which is contacted with the crude extract in step (b) is preferably in a growth phase and in contact with a microbiological nutrient medium. The mixture resulting from step (b) is preferably incubated for a predetermined period of time both to allow the transformation phenomenon to occur and to allow the transformant population to increase to an easily detectable level.

The distinguishing feature possessed by the specific microorganism to be detected relative to the variant may be its ability or inability to grow in contact with a particular microbiological medium or an environment having a particular temperature. Thus, the variant may be an auxotroph or a mutant which is sensitive or resistant to a particular antibiotic or to a particular temperature level.

The preferred method for obtaining the sterile, crude extract of DNA is by the lysis of substantially all of the microorganism cells present in the sample, preferably through the treatment of the samples with a surfactant.

DESCRIPTION OF THE PREFERRED EMBODIMENTS

The surprising feature of the present invention is the finding that crude, cell-extracts of DNA can specifically induce transformation. The only requirement is that the crude extract be sterile, that is, free of viable microorganism cells. Sterility is critical since any viable cells present in the crude extract, including those of the microorganism being detected, would necessarily be found in the mixture that is analyzed in step (c) of the present method. Also, it is likely that microorganisms other than the one under determination which are present in the sample possess the characteristic that is lacking in the DNA-contacted variant. The presence of the distinguishing characteristic in the mixture analyzed in step (c) can be attributed solely to the presence of transformant cells only if the crude extract is completely devoid of viable cells so that any interferring response due to the coincidental presence of the distinguishing characteristic in such extraneous cells can be recognized as such.

At most, two basic manipulative steps are involved in obtaining the sterile, crude extract of DNA. Where viable cells remain in the extract in sufficient numbers to cause interference in the detection of transformant cells in step (c), the remaining viable cells are separated from the extract solution such as by filtering or centrifuging. The preferred method, however, requires only one manipulative step, the lysis of substantially all of the microorganism cells present in the sample. In the lysis of a cell not only is endogenous DNA released, but also the cell wall is ruptured, thereby destroying the cell. Therefore, by lysing substantially all of the cells present, a sterile extract is obtained.

Cell lysis can be accomplished by chemical or physical means, or by a combination of both. Several conventional mechanical means of effecting lysis are available including ultrasonication, use of a French press, and grinding with abrasives such as sand.

The chemical means of lysing microorganism cells are preferred due to their simplicity. The chemical lysis of microorganism cells may be effected through the use of surfactants and/or other agents which act upon the cell surface to cause the chemical breakdown of the cell wall or cause the cell to rupture by reducing the external osmotic pressure exerted on the cell wall. Exemplary of lysiing agents which cause the chemical breakdown of lysing cell walls are various enzymes such as lysozyme and various reagents and reagent mixtures such as a mixture of tri-iso-propyl-naphthalene sulfonate and 4-aminosalicylate. Useful surfactants include both ionic materials, such as polyoxyalkylene derivatives of sorbitan nonolaureate and sorbitan monooleate, and non-ionic materials, such as iso-octyl-phenoxypolyethoxyethanol. A particularly preferred surfactant is sodium dodecyl sulfate.

When a surfactant is employed to lyse the microorganism cells in the sample, as is preferred, it is also preferred that the conditions for the contact between the variant and the crude extract containing the surfactant are such that a substantial amount of the variant cells are not destroyed by the surfactant. A most appropriate manner of forming the variant/crude extract mixture to accomplish this has been found. Before contacting the variant with the crude extract of DNA, the variant is placed on the surface of a microbiological nutrient medium capable of diffusing aqueous solutions which come into contact with a surface of the medium. A concentration of surfactant is used in the DNA extraction step which is sufficiently high to release endogenous DNA from the sample cells, and sufficiently low so that upon accomplishing step (b), a substantial number of the variant cells are not destroyed by the surfactant solution as it diffuses into the medium which supports the variant. Conventional nutrient gels such as agar usually possess such a diffusing characteristic. For most of the conventional surfactants, the preferred concentration range is between about 0.01 and 0.1 percent by weight. This concentration range is particularly useful where the surfactant is sodium dodecyl sulfate.

In step (b) the variant is preferably growing in contact with a suitable microbiological nutrient medium, and the variant/crude extract of DNA mixture is preferably incubated for a predetermined time. These conditions insure that a sufficient number of variant cells pass through a competent growth state (i.e. a stage in which absorbed DNA is able to induce genetic transformation) so that transformant cells appear in easily detectable quantities.

Any transformable variant which is genetically distinguishable from its parent strain may be used in the present method to detect its parent strain. The specific microorganism to be detected may possess one or more distinguishing characteristics relative to the variant used. Variants which may be used in the present method include spontaneous variants and artificially induced mutants. In the isolation of mutants, any of the conventional chemical or physical mutagens or their combination may be employed. Chemical mutagenesis may involve the use of such conventional reagents as the acridines, alkylating agents, hydroxylamine, nitrous acid, 5-bromouracil, 2-aminopurine, and ethyl ethanesulfonate. Conventional physical mutagenesis generally involves irradiation such as with either ultra-violet light or X-rays.

The exact nature of the analysis used in step (c) of the present method depends on the particular distinguishing characteristic of the microorganism under determination relative to the particular variant used. Where the variant and the microorganism to be detected differ in more than one respect, any one of the distinguishing characteristics may be chosen as the one to be detected in step (c). The distinguishing characteristic between the specific microorganism to be determined and the variant usually is either a differing ability to grow in contact with a particular microbiological nutrient medium or an environment having a particular temperature. Two classes of conventionally obtainable variants which are preferably used in the present method are (1) auxotrophs and (2) mutants which are either sensitive or resistant to antibiotics or temperature relative to their parent strain. The exact form of the analysis followed in step (c) of the present method depends on the distinguishing characteristic between the variant and the microorganism being detected.

When the distinguishing characteristic is the fact that the transformant is capable of growing upon contacting a particular microbiological medium whereas the variant is not, step (c) is accomplished by contacting the mixture formed in step (b) with that particular microbiological medium and detecting the development of microbiological growth. If such growth is detected, transformant cells are present, thereby indicating the presence of the specific microorganism to be detected in the sample. Auxotrophs are particularly useful in this scheme since they require one or more nutrients not required by the prototroph. Thus, the particular microbiological medium to be used in detecting the distinguishing characteristic in the mixture from step (b) is a minimal medium containing all of the nutrients required by the prototroph for growth while lacking at least one of the nutrients required by the auxotroph.

Another generally occurring distinguishing characteristic between the specific microorganism to be detected and the variant is the fact that the transformant is capable of growing in contact with a microbiological medium in an environment having a particular temperature while the variant is not, that is, the variant is temperature-sensitive. In such an instance, step (c) is accomplished by placing the mixture formed in step (b) in an environment having that particular temperature and detecting the development of any microbiological growth. If such growth is detected, transformant cells are present, thereby indicating the presence of the specific microorganism to be detected in the sample.

The detection of the development of microbiological growth in the mixture formed in step (b) of the present method, or in the control where decreased growth development is to be detected, may be accomplished by any conventional method using any conventional means. The simplest manner of detecting growth development is by the observation of colony formation either visually, such as by direct observation or with the aid of a microscope, or using instrumental means, such as an automatic colony counter. Another method of detecting growth development involves the use of indicators responsive to the presence of microorganisms. Such indicators include chromogenic indicators such as phenol red, and other reagents, such as 2,3,5-triphenyltetrazolium chloride. The indicator response, which may be chemical or physical, can be observed visually in many cases, such as where chromogenic indicators are used, or by instrumental means. The indicator is incorporated with the microbiological medium with which the mixture formed in step (b) is contacted and its response is then observed. Where the microbiological medium used to contact the mixture found in step (b) is in a liquid form, the turbidity of the medium, being a function of microbiological growth, can be observed visually or by instrumental means as a method for detecting the development of microbiological growth.

It should be noted that the mixture formed in step (b) need not always be contacted with a microbiological medium and the development of microbiological growth detected in order to accomplish step (c). Since the purpose of step (c) is to detect the presence of transformant cells, any means may be used so long as transformant cells can be detected thereby. It may be possible to chemically or physically analyze the mixture formed in step (b) for the repaired gene or for some other characteristic peculiar to the transformant relative to the variant.

While the present method may involve many variations, the following method is most preferred as it is the simplest to perform and involves relatively few manipulations all of which involve standard microbiological techniques. This particularly preferred method comprises the steps of: (a) treating the sample with an aqueous solution of a surfactant in a sufficiently high concentration to lyse substantially all of the microorganism cells present in the sample, thereby releasing endogenous DNA in the form of a sterile, crude extract thereof, such surfactant being in a sufficiently low concentration so that upon contacting the crude extract with a number of microorganism cells growing on the surface of a microbiological medium capable of diffusing aqueous solutions which come into contact with a surface thereof, a substantial number of the cells are not destroyed by the solution of surfactant as it diffuses into the medium; (b) contacting the crude extract with cells of an auxotroph of the specific microorganism to be detected, which cells are growing on the surface of a complete microbiological medium, the complete medium containing all of the nutrients required by the auxotroph for growth and being capable of diffusing aqueous solutions which come into contact with a surface thereof; (c) incubating the resulting mixture for a predetermined period of time; (d) transferring at least a portion of the resulting incubated mixture to a minimal microbiological medium containing all of the nutrients required by the prototroph of the auxotroph for growth while lacking at least one of the nutrients required by the auxotroph for growth; and (e) detecting the development of microbiological growth of the portion of the resulting incubated mixture transferred to the minimal microbiological medium, the development of microbiological growth indicating the presence in the sample of the specific microorganism to be detected.

All microorganisms for which transformable variants can be obtained may be detected using the present method. A transformable variant is one which is itself competent or which can be artificially induced to competency. A competent microorganism cell is one which is able to take up a molecule of transforming DNA and to be transformed thereby. At the present time, it is unknown what causes one type of variant to be competent while another is not. There is some evidence that the presence of particular proteinaceous materials in certain cells provide those cells with the transformation mechanism. The present method is not limited to the use of variants which are presently known to be competent, but extends to those found to be competent in the future as well as those which can be induced to competency. At the present time various types and classes of microorganisms for which competent variants have been obtained include various algaes and bacteria such as Moraxella, Pneumococcus, Haemophilus, Streptococcus, Staphylococcus, Bacillus, Neisseria, Rhizobium, and Acinetobacter. The term microorganism as used herein refers to a wide variety of macroscopic and microscopic living matter including algae, fungi such as yeast, and bacteria.

Various biological samples may be assayed using the present method. Both pure isolates and heterogenous samples may be assayed. As a clinical method, assayable biological samples include urine, serum, tissue swabs, sputum, and cerebral and spinal fluids. Pure colony isolates of these substances may also constitute the assayed sample. While the prior art requires the use of pure, homogenous isolates, the present method can be used to assay heterogenous samples, that is, samples containing extraneous microorganisms and other extraneous substances, since DNA-transformation is absolutely specific and the present invention discloses the use of crude extracts of DNA to cause transformation.

The present invention will now be illustrated, but is not intended to be limited, by the following example.

EXAMPLE

This example illustrates in detail the present method for use in detecting Acinetobacter strains wherein the microorganism cells in the sample are lysed with a surfactant and wherein the mutant is an auxotroph.

A. Preparation of Transforming Deoxyribonucleic Acid

A biological sample which is to be assayed for the presence of a specific microorganism, such as a loopful of a cell paste harvested from the surface of a conventional growth medium, is suspended in a sterile solution containing 0.05% sodium dodecyl sulfate in standard saline citrate (0.15M sodium chloride, 0.015M sodium citrate). The exact volume of the surfactant solution varies with the size of the biological sample; however, as a point of reference, 0.5 ml of solution is usually used for each loopful of cell paste. The resulting suspension is stirred in an orbital mixer with care being taken to avoid adherence of the sample to the tube containing the suspension above the level of the liquid. The suspension is then heated in a water bath at about 60°C for about 1 hour (as short a time as 5 minutes has been found to be sufficient). At this point, substantially all of the microorganism cells in the sample have been lysed, resulting in a sterile, crude DNA solution. Such extracts have been found to be stable for periods exceeding 1 year at between 3° and 5°C.

B. Preparation of a Stable, Competent Auxotroph

Auxotrophic mutants can be obtained by N-methyl-N'-nitro-N-nitrosoguanidine mutagenesis as described by Adelberg, Mendel, and Chen in *Biochem. Biophys. Res. Commun.* 18: 788–95(1965). Auxotrophs prepared in this manner have been found to require minimal medium containing a certain amount of amino acids such as isoleucine, valine, and leucine not required by the wild, parent strain. The stability of auxotrophs prepared in this manner may be tested by attempting to revert them to prototrophy with chemical mutagens using the auxanographic procedure described by Iyer and Szybalski in *Appl. Microbiol.* 6:23–9(1958). Auxotrophs which readily revert spontaneously when plated on minimal medium should be rejected without further analysis by this method.

C. Preparation of Minimal and Complete Media

Minimal agar is prepared by mixing equal parts of 3% agar and "S-2" salts solution of Monod and Wollman as described in *Ann. Inst. Pasteur* 73:937–56(1947) (or any other conventional mineral medium) followed by the addition of the appropriate amount of a 50% solution of a carbon source to give a final concentration 0.25%. Carbon sources suitable for growth of competent strains of Acinetobacter include D,L-lactic acid, L-malic acid, glucose, and 2,3-butanediol. Complete media may be prepared by adding the amino acids required by the auxotroph to minimal media in a concentration of about 100 µg/ml or conventional media such as heart infusion media may be used.

D. Transformation Assay

A small amount of cell paste of a stable auxotroph of Acinetobacter, just visible to the naked eye, is applied to a sector of a plate containing a complete medium. A loopful of the crude extract containing DNA, as prepared in procedure a. above, is used to suspend and spread the cell paste over an area of about 5 to 10 mm in diameter. Cell paste of the auxotroph is also spread on another sector of the same plate to serve as a non-DNA-treated control. A third sector of the plate is streaked with a loopful of the DNA preparation in order to test its sterility.

The plate is incubated for about 12 to 24 hours (shorter periods down to about 1 hour may be used) at about 35°C and the growth resulting from the DNA-treated auxotroph cell paste is streaked heavily on a sector of a plate containing a minimal medium. The plate is incubated at about 35°C. After between about 12 and 24 hours, all auxotrophic cells which have been transformed to prototrophy will appear as colonies visible to the naked eye. A low power lens or dissecting microscope can be used for recognition of transformant colonies after shorter periods of incubation. Auxotrophs which are treated with DNA extracted from microorganisms of the Acinetobacter genus will result in the appearance of prototrophic transformant colonies, whereas cells mixed with DNA from an unrelated microorganism will show no colonies on the minimal plate. Further details may be found in *J. Bacteriol.* 112(2):917–31(1972).

What is claimed is:

1. A method for detecting the presence of a specific microorganism in a biological sample comprising the steps o:
   a. contacting said biological sample with an aqueous solution containing a surfactant capable of lysing microorganism cells present in said biological sample to form a sterile, crude, aqueous extract comprising endogenous deoxyribonucleic acid;
   b. contacting a viable, transformable variant of said specific microorganism with said crude extract to form a mixture, said specific microorganism possessing a distinguishing characteristic relative to said variant, said variant being supported on a microbiological medium capable of diffusing aqueous solutions; and
   c. subjecting said mixture to an analysis for detecting the presence of said distinguishing characteristic;
   said surfactnat in step (a) being present in said aqueous solution at a concentration sufficient to lyse substantially all of the microorganism cells present in said biological sample while sufficient to destroy a substantial amount of said variant upon contacting said variant with said crude extract in step (b) and during the diffusion of said crude, aqueous extract into said microbiological medium.

2. A method as in claim 1 which comprises the additional step of incubating the mixture resulting from step (b) for a predetermined period of time.

3. A method as in claim 1 wherein said specific microorganism is selected from the group consisting of Moraxella, Pneumococcus, Haemophilus, Streptococcus, Staphylococcus, Bacillus, Neisseria, Rhizobium, and Acinetobacter.

4. A method as in claim 1 wherein said surfactant is in a concentration of between about 0.01 and 0.1 percent by weight.

5. A method as in claim 4 wherein said surfactant is sodium dodecyl sulfate.

6. A method as in claim 5 wherein sodium dodecyl sulfate is in a concentration of about 0.05 percent by weight.

7. A method as in claim 1 wherein said distinguishing characteristic is the fact that said variant and its transformant differ in their ability to grow upon contacting a particular microbiological medium.

8. A method as in claim 7 wherein said transformant is capable of growing upon contacting said particular microbiological medium whereas the variant is not and wherein step (c) is accomplished by contacting said mixture with said particular microbiological medium and detecting the development of microbiological growth, the development of microbiological growth indicating the presence of said specific microorganism in said biological sample.

9. A method as in claim 8 wherein said variant is a mutant.

10. A method as in claim 9 wherein said mutant is an auxotroph of said specific microorganism and wherein said particular microbiological medium is a minimal medium containing all of the nutrients required by the prototroph of said auxotroph for growth while lacking at least one of the nutrients required by said auxotroph for growth.

11. A method as in claim 8 wherein said detection of the development of microbiological growth is accomplished by an observation of colony formation.

12. A method as in claim 11 wherein said observation is accomplished visually.

13. A method as in claim 11 wherein said observation is accomplished by instrumental means.

14. A method as in claim 8 wherein said particular microbiological medium comprises an indicator responsive to the presence of microorganisms and wherein the indicator response is observed visually or by instrumental means.

15. A method as in claim 8 wherein said particular microbiological medium is in a liquid form and wherein said detection of the development of microbiological growth is accomplished by observing the turbidity of said particular microbiological medium.

16. A method as in claim 15 wherein said turbidity is observed by instrumental means.

17. A method as in claim 1 wherein said distinguishing characteristic is the fact that said variant and its transformant differ in their ability to grow in an environment having a particular temperature.

18. A method as in claim 17 wherein said transformant is capable of growing in contact with a microbiological medium in an environment having said particular temperature whereas the variant is not and wherein step (c) is accomplished by placing said mixture in an environment having said particular temperature and detecting the development of microbiological growth, the development of microbiological growth indicating the presence of said specific microorganism in said biological sample.

19. A method as in claim 17 wherein said detection of the development of microbiological growth is accomplished by an observation of colony formation.

20. A method as in claim 19 wherein said observation is accomplished visually.

21. A method as in claim 19 wherein said observation is accomplished by instrumental means.

22. A method as in claim 17 wherein said particular microbiological medium comprises an indicator responsive to the presence of microorganisms and wherein the indicator response is observed visually or by instrumental means.

23. A method as in claim 17 wherein said particular microbiological medium is in a liquid form and wherein said detection of the development of microbiological growth is accomplished by observing the turbidity of said particular microbiological medium.

24. A method as in claim 23 wherein said turbidity is observed by instrumental means.

25. A method for detecting the presence of a specific microorganism in a biological sample comprising the steps of:
   a. treating said biological sample with an aqueous solution of a surfactant which is in a sufficiently high concentration to lyse substantially all of the microorganism cells present in said sample and thereby release endogenous deoxyribonucleic acid in the form of a sterile, crude extract thereof, said surfactant being in a sufficiently low concentration so that upon contacting said crude extract with a number of microorganism cells growing on the surface of a microbiological medium capable of diffusing aqueous solutions which come into contact with a surface thereof, a substantial number of the cells are not destroyed by the solution of surfactant as it diffuses into the medium;
   b. contacting said crude extract with cells of an auxotroph of said specific microorganism, which cells are growing on the surface of a complete microbiological medium, said complete medium containing all of the nutrients required by said auxotroph for growth and being capable of diffusing aqueous solutions which come into contact with a surface thereof.

c. incubating the resulting mixture for a predetermined period of time.

d. transferring at least a portion of the resulting incubated mixture to a minimal microbiological medium containing all of the nutrients required by the prototroph of said auxotroph for growth but lacking at least one of the nutrients required by said auxotroph for growth, and e. detecting the development of any microbiological growth of the portion of said resulting incubated mixture transferred to said minimal microbiological medium, the development of microbiological growth indicating the presence of said specific microorganism in said biological sample.

26. A method as in claim 25 wherein said surfactant is in a concentration of between about 0.01 and 0.1 percent by weight.

27. A method as in claim 26 wherein said surfactant is sodium dodecyl sulfate.

28. A method as in claim 27 wherein sodium dodecyl sulfate is in a concentration of about 0.05 percent by weight.

29. A method as in claim 25 wherein step (e) is accomplished by an observation of colony formation.

30. A method as in claim 29 wherein said observation is accomplished visually.

31. A method as in claim 29 wherein said observation is accomplished by instrumental means.

32. A method as in claim 25 wherein said minimal microbiological medium comprises an indicator responsive to the presence of microorganisms and wherein the indicator response is observed visually or by instrumental means.

33. A method as in claim 25 wherein said minimal microbiological medium is in a liquid form and wherein step (e) is accomplished by observing the turbidity of said minimal microbiological medium.

34. A method as in claim 33 wherein said turbidity is observed by instrumental means.

* * * * *

PO-1050
(5/69)

UNITED STATES PATENT OFFICE
CERTIFICATE OF CORRECTION

Patent No. 3,930,956               Dated January 6, 1976

Inventor(s)   Elliot Juni

It is certified that error appears in the above-identified patent and that said Letters Patent are hereby corrected as shown below:

Column 1, line 42, "maned" should read --named--.

Column 4, line 24, "breakdown of lysing cell walls are various enzymes" should read --breakdown of the cell walls are various enzymes--.

Column 4, line 29, "nonolaureate" should read --monolaureate--.

Column 9, line 3, "o" should read --of--.

Column 9, line 18, "surfactnat" should read --surfactant--.

Column 9, line 21, "sufficient" should read --insufficient--.

Signed and Sealed this

Sixth Day of July 1976

[SEAL]

Attest:

RUTH C. MASON
*Attesting Officer*

C. MARSHALL DANN
*Commissioner of Patents and Trademarks*

PO-1050
(5/69)

UNITED STATES PATENT OFFICE
CERTIFICATE OF CORRECTION

Patent No. 3,930,956     Dated January 6, 1976

Inventor(s) Elliot Juni

It is certified that error appears in the above-identified patent and that said Letters Patent are hereby corrected as shown below:

Column 10, line 29, "17" should read --18--.

Column 10, line 36, "17" should read --18--.

Column 10, line 41, "17" should read --18--.

Signed and Sealed this

Twenty-eighth Day of September 1976

[SEAL]

Attest:

RUTH C. MASON
*Attesting Officer*

C. MARSHALL DANN
*Commissioner of Patents and Trademarks*